(12) United States Patent
Terauchi et al.

(10) Patent No.: US 8,421,007 B2
(45) Date of Patent: Apr. 16, 2013

(54) X-RAY DETECTION SYSTEM

(75) Inventors: Masami Terauchi, Miyagi (JP); Takanori Murano, Tokyo (JP); Nobuo Handa, Tokyo (JP); Hideyuki Takahashi, Tokyo (JP)

(73) Assignees: Tohoku University, Miyagi (JP); JEOL Ltd., Tokyo (JP)

( * ) Notice: Subject to any disclaimer, the term of this patent is extended or adjusted under 35 U.S.C. 154(b) by 0 days.

(21) Appl. No.: 13/110,214

(22) Filed: May 18, 2011

(65) Prior Publication Data

US 2012/0292508 A1 Nov. 22, 2012

(51) Int. Cl.
*H01J 40/00* (2006.01)

(52) U.S. Cl.
USPC ............................... 250/305; 250/310

(58) Field of Classification Search .................. 250/305, 250/306, 307, 310, 311
See application file for complete search history.

(56) References Cited

U.S. PATENT DOCUMENTS

| | | | | |
|---|---|---|---|---|
| 5,590,168 A | * | 12/1996 | Iketaki | 378/43 |
| 5,650,616 A | * | 7/1997 | Iketaki | 250/288 |
| 6,195,410 B1 | * | 2/2001 | Cash, Jr. | 378/43 |
| 6,522,717 B1 | * | 2/2003 | Murakami et al. | 378/43 |
| 7,961,379 B2 | * | 6/2011 | Shigekawa et al. | 359/331 |
| 2002/0050564 A1 | * | 5/2002 | Birk et al. | 250/306 |
| 2004/0061051 A1 | * | 4/2004 | Schneiker et al. | 250/306 |
| 2005/0045821 A1 | * | 3/2005 | Noji et al. | 250/311 |
| 2007/0057184 A1 | * | 3/2007 | Uto et al. | 250/310 |
| 2007/0210250 A1 | * | 9/2007 | Ward et al. | 250/307 |
| 2008/0061227 A1 | * | 3/2008 | Kovtoun | 250/292 |
| 2011/0174973 A1 | * | 7/2011 | DeWalch | 250/310 |
| 2011/0204228 A1 | * | 8/2011 | Tsuno et al. | 250/310 |
| 2011/0291010 A1 | * | 12/2011 | Katane et al. | 250/310 |

FOREIGN PATENT DOCUMENTS

JP 2002329473 A 11/2002

OTHER PUBLICATIONS

Ghiringhelli et al., Saxes a High Resolution Spectrometer for Resonant X-Ray Emission in the 400-1600eV Energy Range, Nov. 14 2006, Review of Scientific Instruments, 77,113108.*

* cited by examiner

*Primary Examiner* — Robert Kim
*Assistant Examiner* — Jason McCormack
(74) *Attorney, Agent, or Firm* — The Webb Law Firm (57) ABSTRACT

An X-ray detection system has an electron beam irradiation portion, a diffraction grating, a splitter for distributing the direction of propagation of the diffracted X-rays such that an imaging plane for the diffracted X-rays is assigned to plural positions spaced apart in a direction perpendicular to the direction of energy dispersion of the diffracted X-rays, and image sensors different in energy sensitivity disposed respectively at the positions to which the imaging plane is assigned.

5 Claims, 10 Drawing Sheets

X-RAY DETECTION SYSTEM

BACKGROUND OF THE INVENTION

1. Field of the Invention

The present invention relates to an X-ray detection system and, more particularly, to an X-ray detection system which, when it is attached to a scanning electron microscope and soft X-rays are spectroscopically analyzed, is able to measure a wide energy range.

2. Description of the Related Art

When a charged-particle beam such as an electron beam is directed at a sample, characteristic X-rays are emitted from the sample. The characteristic X-rays are detected by a detector, and the composition of the sample is measured. This technique is known as energy dispersive X-ray spectroscopy and makes use of the phenomenon that characteristic X-rays have energies intrinsic to elements constituting the sample. The number of X-rays produced per unit time is counted for each energy of the X-rays and thus information about the constituent elements of the sample is obtained. Usually, a semiconductor detection device using a semiconductor crystal such as silicon or germanium is used as a means for detecting X-rays.

On the other hand, there exists an imaging technique. In particular, a sample is irradiated with a charged-particle beam such as an electron beam. The resulting characteristic X-rays are made to impinge on a diffraction grating. As a result, diffracted X-rays are separated. The diffracted X-rays are detected by an X-ray CCD image sensor, whereby the X-rays are imaged.

An instrument for implementing this technique is designed including an electron beam irradiation portion for irradiating a sample with an electron beam, a diffraction grating with unequal pitch (varied line-space (VLS) diffraction grating), an X-ray focusing mirror for focusing the characteristic X-rays emitted from the irradiated sample and directing the X-rays toward the grating which receives the focused characteristic X-rays and produces diffracted X-rays, and an image sensor (back-illuminated CCD camera) for detecting the diffracted X-rays.

An X-ray detection system of this type is also described in patent document 1 (described below).

PRIOR ART REFERENCES

Patent Documents

Patent Document 1: JP-A-2002-329473

First Problem

In the X-ray detection system described, for example, in the above-cited patent document 1, high-resolution measurements are enabled with a compact optical system. On the other hand, in order to vary the energy region to be measured, it is necessary to exchange the image sensor. However, it has not been easy to make such an exchange because the X-ray detection system is mounted in a vacuum.

Second Problem

When a sample made of a compound of an oxide, nitride, or other material is irradiated with an electron beam by the use of the X-ray detection system described so far, cathodoluminescence light different in wavelength from the characteristic X-rays is produced besides the characteristic X-rays. The cathodoluminescence light is reflected nearly totally by the diffraction grating and impinges on the image sensor. As a result, the relative level of the signal of the diffracted X-rays drops on the image sensor, making the collected spectrum obscure. This will adversely affect the measurement time and the measurement accuracy. In this case, it is desired that the diffracted X-rays and the cathodoluminescence light can be separated from each other. Unfortunately, there exists the problem that there is not any filter adapted to separate them from each other.

SUMMARY OF THE INVENTION

In view of the foregoing problems, the present invention has been made. It is an object of the invention to provide an X-ray detection system in which characteristic X-rays emitted from a sample irradiated with an electron beam are diffracted by a diffraction grating and a spectrum is collected by image sensors and which is capable of measuring a wide energy region.

It is another object of the invention to provide an X-ray detection system in which characteristic X-rays emitted from a sample irradiated with an electron beam are diffracted by a diffraction grating and a spectrum is collected by image sensors and in which the ratio of X-rays impinging on the image sensors can be increased.

(1) A first embodiment of the present invention provides an X-ray detection system comprising electron beam irradiation means for irradiating a sample with an electron beam, a diffraction grating that receives characteristic X-rays emitted from the irradiated sample and produces diffracted X-rays, a splitter for distributing the direction of propagation of the diffracted X-rays such that an imaging plane for the diffracted X-rays is assigned to plural positions spaced apart in a direction perpendicular to the direction of energy dispersion of the diffracted X-rays, and plural image sensors disposed respectively at the plural positions to which the imaging plane is assigned, the image sensors having different energy sensitivities.

(2) A modification of the first embodiment (1) is characterized in that the splitter has a tubular X-ray guiding mirror portion made of mirrors for reflecting the diffracted X-rays and including a branching portion, a movable mirror portion for distributing the direction of propagation of the diffracted X-rays in the branching portion of the X-ray guiding mirror portion, and a movable mirror controller for controlling the position of the movable mirror portion.

(3) Another X-ray detection system is based on any one of (1) and (2) above and characterized in that one of the plural image sensors has a higher energy sensitivity and is an X-ray image sensor and that the other has a lower energy sensitivity and has a microchannel plate subassembly on its light-sensitive surface.

(4) A second embodiment of the invention provides an X-ray detection system comprising electron beam irradiation means for irradiating a sample with an electron beam, a diffraction grating that receives characteristic X-rays emitted from the irradiated sample and produces diffracted X-rays, a microchannel plate subassembly having an input surface located at an imaging plane for the diffracted X-rays, and an image sensor disposed on the output surface of the microchannel plate subassembly.

(5) A further X-ray detection system is based on any one of (3)-(4) above and characterized in that the microchannel plate subassembly has a higher quantum efficiency in the soft X-ray region than in a cathodoluminescence region.

(6) An additional X-ray detection system is based on any one of (3)-(5) above and characterized in that there are further provided: a tiltably-and-rotatably holding portion for holding the microchannel plate subassembly such that it is rotatable while being tilted relative to the direction of propagation of the diffracted X-rays; and a rotation control portion for rotating the microchannel plate subassembly while the subassembly is held by the tiltably-and-rotatably holding portion.

(7) A yet other X-ray detection system is based on any one of (1)-(6) above and characterized in that the diffraction grating is a varied line-space (VLS) diffraction grating.

These embodiments of the present invention can yield the following advantageous effects.

(A) In the first embodiment, characteristic X-rays emitted from the sample irradiated with the electron beam are received by the diffraction grating. As a result, diffracted X-rays are produced. The direction of propagation of the diffracted X-rays is distributed by the splitter such that the imaging plane for the diffracted X-rays is assigned to the plural positions spaced apart in the direction perpendicular to the direction of energy dispersion of the diffracted X-rays produced by the diffraction grating. Consequently, the imaging plane at which the diffracted X-rays are focused is distributed. The plural image sensors having different energy sensitivities are disposed respectively at the plural positions to which the imaging plane is assigned. Hence, an X-ray detection system capable of measuring a wide energy region can be accomplished.

(B) The splitter can distribute the direction of propagation of the diffracted X-rays by having the tubular X-ray guiding mirror portion made of the mirrors for reflecting the diffracted X-rays, the movable mirror portion for distributing the direction of propagation of the diffracted X-rays in the branching portion of the guiding mirror portion, and the movable mirror control portion for controlling the position of the movable mirror portion. In consequence, the imaging plane for the diffracted X-rays can be distributed according to the energy region.

(C) A wide energy region can be measured by disposing an X-ray image sensor as the image sensor having the higher energy sensitivity and disposing an image sensor having a microchannel plate subassembly on its light-sensitive surface as the image sensor having the lower energy sensitivity.

(D) In the second embodiment of the invention, characteristic X-rays emitted from the sample irradiated with the electron beam are received by the diffraction grating. This gives rise to diffracted X-rays. The input surface of the microchannel plate subassembly is disposed at the imaging plane for the diffracted X-rays. The image sensor is disposed on the output surface of the microchannel plate subassembly, which has a higher quantum efficiency in the soft X-ray region than in the cathodoluminescence region. If cathodoluminescence is generated, the ratio of X-rays impinging on the image sensors can be increased.

(E) In an X-ray detection system using the microchannel plate subassembly described thus far, the microchannel plate subassembly is held rotatably while being tilted relative to the direction of propagation of the diffracted X-rays. Maximum sensitivity characteristics can be imparted to the microchannel plate subassembly whose sensitivity depends on the angle of incidence by rotating the microchannel plate subassembly in a controlled manner. Consequently, the ratio of the X-rays impinging on the image sensors can be increased.

(F) By using a varied line-space (VLS) diffraction grating as a diffraction grating having any or some of the features (A)-(E) above, aberration correction is made when the X-rays enter at a large angle of incidence close to parallelism (close to 90°). Also, an imaging plane perpendicular to the diffracted X-rays can be accomplished.

Other features and advantages of the present invention will become apparent from the following more detailed description, taken in conjunction with the accompanying drawings, which illustrate, by way of example, the principles of the invention.

DETAILED DESCRIPTION OF THE INVENTION

Embodiments for implementing imaging apparatus of the present invention are hereinafter described in detail with reference to the drawings.

First Embodiment

Figure 1:
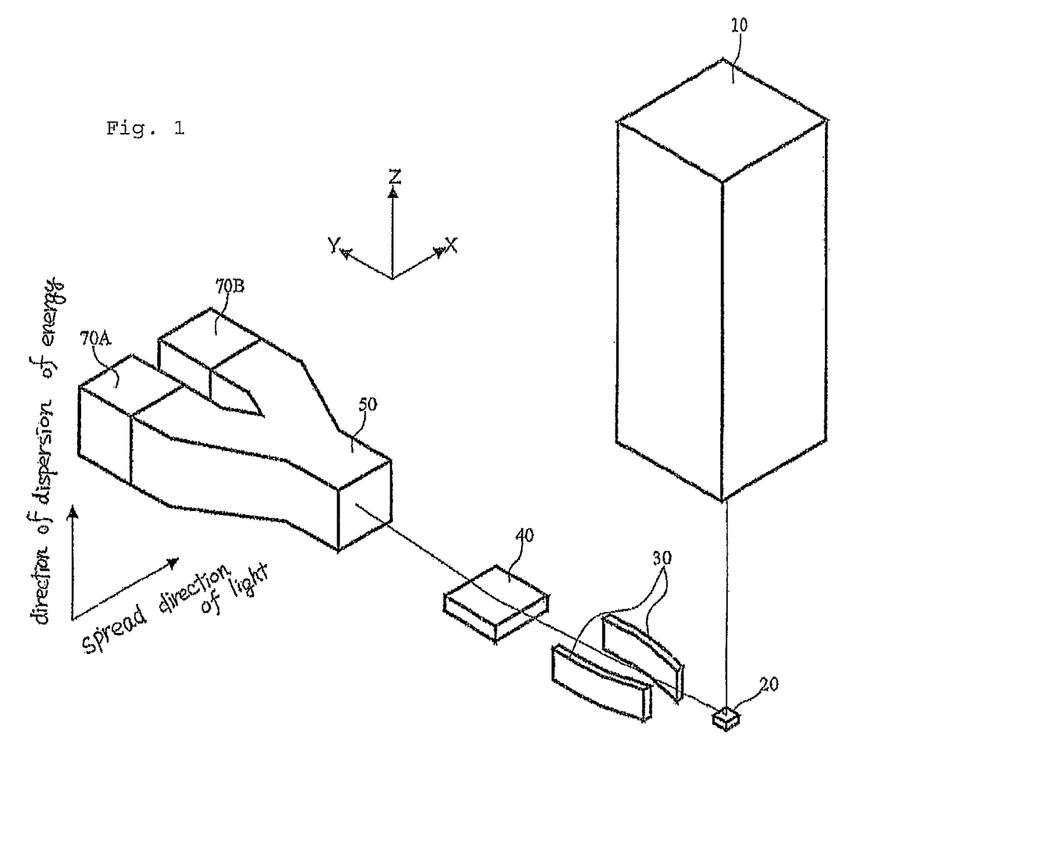
FIG. 1 is a perspective view of an X-ray detection system according to one embodiment of the present invention, showing the structure of the system.
Figure 2A:
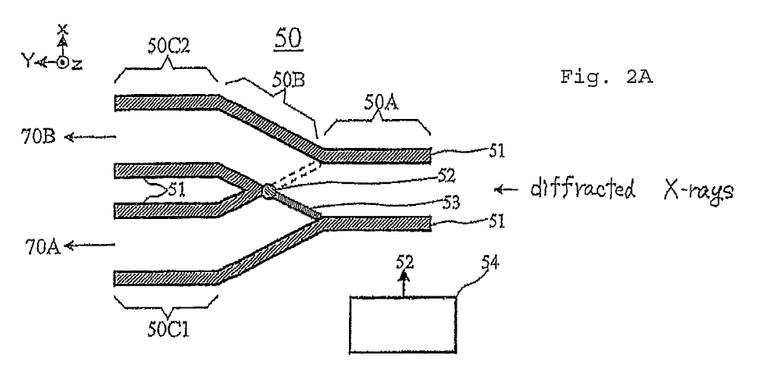
FIGS. 2A-2D are cross sections of main portions of the X-ray detection system shown in FIG. 1.
Figure 2B:
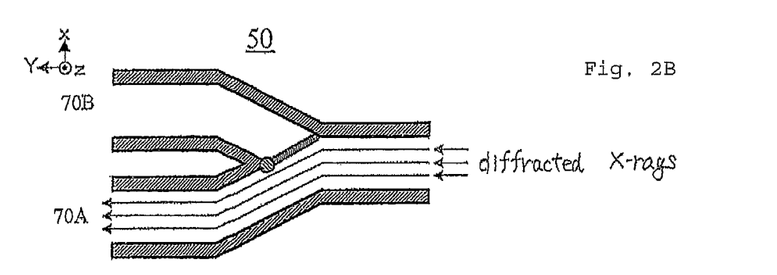
Figure 2C:
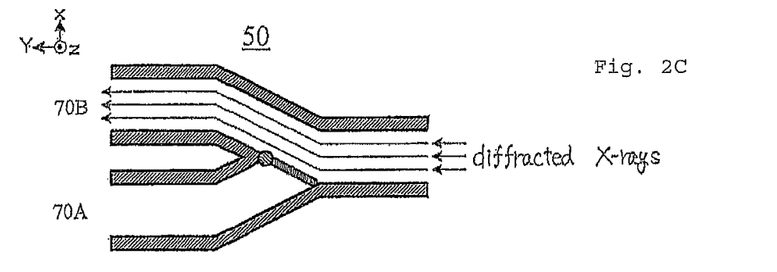
Figure 2D:
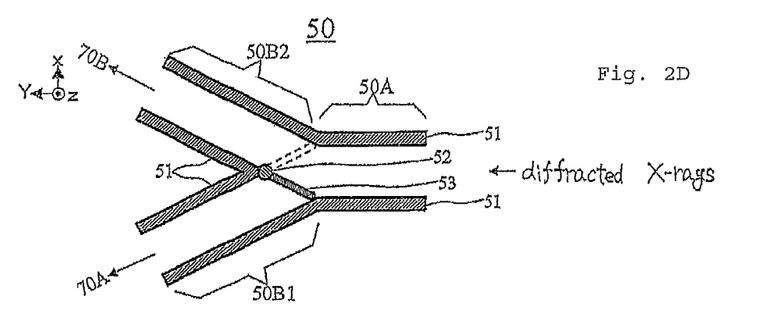

The configuration of an X-ray detection system according to a first embodiment is first described by referring to FIGS. 1-2D.

In FIG. 1, well-known fundamental members for holding electron-optical column, pedestal, and so on, and mechanical portions for maintaining a vacuum are omitted. The following description centers on the arrangement of characteristic portions of the embodiment.

The X-ray detection system includes an electron beam irradiation portion 10 mounted in the electron optical column of a scanning electron microscope and directs an electron beam at a sample 20. As a result, the sample 20 produces characteristic X-rays.

The system further includes an X-ray gathering mirror portion 30 having two mirrors which guide the characteristic X-rays toward a diffraction grating 40. The X-rays are gathered by the mirror portion 30. This increases the intensity of the characteristic X-rays hitting the diffraction grating 40. Consequently, the measurement time can be shortened and the S/N of the spectrum can be improved.

In response to the characteristic X-rays gathered by the X-ray gathering mirror portion 30, the diffraction grating 40 produces X-rays which are diffracted in a different manner according to different energy. The grating 40 has grooves with unequal spacing for aberration correction. This varied line-space (VLS) diffraction grating 40 is so designed that when X-rays enter at a large angle of incidence close to 90° (i.e., the X-rays are propagating nearly parallel to the plane of the diffraction grating (Y-axis of FIG. 1)), the focus of the diffracted X-rays is not on a Rowland circle but on a plane (light-sensitive surfaces of image sensors 70A and 70B) (hereinafter may be collectively referred to as the image sensor arrangement 70) (XZ-plane of FIG. 1)) substantially perpendicular to the X-rays.

The system further includes a splitter 50 that distributes the direction of propagation of the diffracted X-rays from the diffraction grating 40 such that the imaging plane for the diffracted X-rays is assigned to plural positions spaced apart in a direction (X-direction in FIG. 1) perpendicular to the direction of dispersion (Z-direction in FIG. 1) of energy of the diffracted X-rays.

As shown in FIG. 2A, the splitter 50 is configured including a tubular X-ray guiding mirror portion made by mirrors 51 for reflecting the diffracted X-rays. The guiding mirror portion includes an introduction portion 50A, a branching portion 50B, and branching output portions 50C1 and 50C2. The mirror portion further includes a movable mirror portion 53 for distributing the direction of propagation of the diffracted X-rays in the branching portion 50B of the guiding mirror portion, a movable mirror driving portion 52 for driving the movable mirror portion 53, and a control portion 54 for giving instructions to the movable mirror driving portion 52 such that the position of the movable mirror portion 53 is controlled according to various decision conditions.

As shown in FIG. 2D, the branching portion 50B and branching output portion 50C1 of the splitter 50 may be integrated into a branching portion 50B1 without folding them. Also, the branching portion 50B and branching output portion 50C2 may be integrated into a branching portion 50B2 without folding them. In this case, the number of folds is reduced. There arises the advantage that the X-ray transmission loss in the splitter 50 is reduced.

In the following description, the splitter 50 shown in FIG. 2A is taken as a specific example. In each case, a counterpart of the splitter 50 shaped as shown in FIG. 2D can be replaced by the splitter 50.

The image sensor arrangement 70 including the image sensors 70A and 70B consists of X-ray CCD cameras or CMOS camera of two kinds having higher energy sensitivity and lower energy sensitivity, respectively, to the soft X-rays in order to detect different energy regions of the diffracted X-rays. Preferably, each CCD camera is a back-illuminated X-ray CCD camera. The position of the image sensor arrangement 70 is so adjusted that its sensitive surface agrees with the imaging plane for the diffracted X-rays.

The image sensor 70A is attached to the imaging plane of the splitter 50 on the side of the branching output portion 50C1, while the image sensor 70B is attached to the imaging plane of the splitter 50 on the side of the branching output portion 50C2. The image sensors 70A and 70B are different in energy sensitivity characteristics.

In the configuration described so far, the control portion 54 gives operating instructions to the movable mirror driving portion 52 by referring to decision conditions (such as energy value, kind of the used diffraction grating 40, material of the sample 20 (as to whether it easily produces cathodoluminescence), kind of the used X-ray window, and the ratio of signal intensity between characteristic X-rays and cathodoluminescent signal) and using predetermined decision conditions.

For example, where the control portion 54 has decided to perform a measurement using the image sensor 70A based on these decision conditions, the control portion gives an instruction to the movable mirror driving portion 52 to block the branching output portion 50C2 by the movable mirror portion 53 as shown in FIG. 2B. Consequently, the diffracted X-rays entering from the introduction portion 50A of the splitter 50 are guided toward the branching output portion 50C1 from the branching portion 50B and focused onto the light-sensitive surface of the image sensor 70A. A spectrum of the X-rays diffracted and arising from the sample 20 is collected by the image sensor 70A and thus a measurement is performed.

On the other hand, where the control portion 54 has decided to perform a measurement using the image sensor 70B based on the above-described decision conditions, the control portion gives an instruction to the movable mirror driving portion 52 such that the movable mirror portion 53 blocks off the branching output portion 50C1 as shown in FIG. 2C. Consequently, the diffracted X-rays impinging from the introduction portion 50A of the splitter 50 are guided from the branching portion 50B toward the branching output portion 50C2 and focused onto the light-sensitive surface of the image sensor 70B. As a result, a spectrum of the X-rays diffracted and arising from the sample 20 is collected by the image sensor 70B and thus a measurement is carried out.

To facilitate understanding the motion of the movable mirror portion 53, a gap is shown to be created between each branching output portion and the mirror portion 53 if the branching output portion is closed. Preferably, such a gap or step is minimized.

As described so far, image sensors having different energy sensitivity characteristics are arranged as the image sensors 70A and 70B. An X-ray detection system capable of measuring a wide energy region can be accomplished by distributing the direction of propagation of the diffracted X-rays by means of the splitter 50.

Second Embodiment

Figure 3:
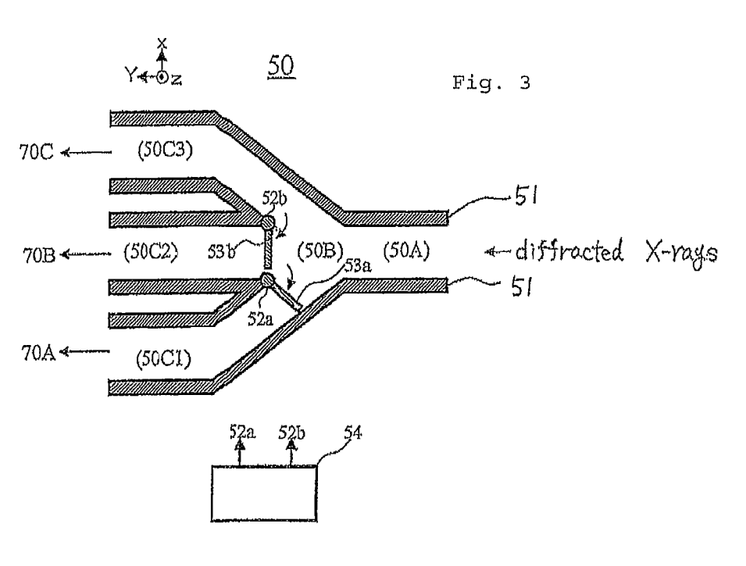
FIG. 3 is across section of a main portion of an X-ray detection system according to an embodiment of the invention.

The configuration of an X-ray detection system according to a second embodiment is described by referring to FIG. 3. In all the FIGS. 1-3, the same components are indicated by the same reference numerals and repeated description thereof will be omitted.

The second embodiment is similar to the first embodiment except for the number of positions to which the X-rays are distributed by the splitter 50. That is, the splitter 50 shown in FIG. 3 distributes the direction of propagation of the diffracted X-rays emitted from the diffraction grating 40 such that the imaging plane for the diffracted X-rays is assigned to three positions spaced apart in a direction (X-direction in FIG. 1) perpendicular to the direction of energy dispersion (Z-direction in FIG. 1) of the diffracted X-rays.

The splitter 50 is configured including a tubular X-ray guiding mirror portion made by mirrors 51 for reflecting the diffracted X-rays. The mirror portion includes an introduction portion 50A, a branching portion 50B, and branching output portions 50C1, 50C2, 50C3. The mirror portion further includes the movable mirror portion 53 for distributing the direction of propagation of the diffracted X-rays in the branching portion 50B of the mirror portion, a movable mirror driving portion 52 (including portions 52a and 52b) for driving the movable mirror portion 53 (including portions 53a and 53b), and a control portion 54 for giving instructions to the movable mirror driving portion 52 such that the position of the movable mirror portion 53 is controlled according to various decision conditions.

The image sensors 70A, 70B, and 70C of the image sensor arrangement 70 are three kinds of X-ray CCD cameras or X-ray CMOS cameras having high, moderate, and low energy sensitivities, respectively, to the soft X-rays in order to detect different energy regions of the diffracted X-rays. Preferably, each image sensor is made of a back-illuminated X-ray CCD camera. The position of the image sensor arrangement 70 is so adjusted that its light-sensitive surface is coincident with the imaging plane for the diffracted X-rays.

The image sensor 70A is mounted at the imaging plane of the splitter 50 on the side of the branching output portion 50C1. The image sensor 70B is mounted at the imaging plane of the splitter 50 on the side of the branching output portion 50C2. The image sensor 70C is mounted at the imaging plane of the splitter 50 on the side of the branching output portion 50C3. The image sensors 70A-70C are different in energy sensitivity characteristics.

In the configuration described so far, the control portion 54 gives operating instructions to the movable mirror driving portion 52 by referring to decision conditions (such as energy value, kind of the used diffraction grating 40, material of the sample 20 (as to whether it easily produces cathodoluminescence), kind of the used X-ray window, and the ratio of signal intensity between characteristic X-rays and cathodoluminescent signal) and using predetermined decision conditions.

For example, where the control portion 54 has decided to perform a measurement using the image sensor 70C based on these decision conditions, the control portion gives an instruction to the movable mirror driving portions 52a and 52b to block off the branching output portions 50C1 and 50C2 by the movable mirror portions 53a and 52b as shown in FIG. 3.

Consequently, the diffracted X-rays entering from the introduction portion 50A of the splitter 50 are guided toward the branching output portion 50C3 from the branching portion 50B and focused onto the light-sensitive surface of the image sensor 70C. A spectrum of the diffracted X-rays owing to the sample 20 is collected by the image sensor 70C and thus a measurement is performed.

To facilitate understanding the motion of the movable mirror portions 53a and 53b, a gap is shown to be present if the movable mirror portions 53a and 53b are closed. Preferably, such a gap or step is minimized.

As described so far, image sensors having different energy sensitivity characteristics are arranged as the image sensors 70A, 70B, and 70C. An X-ray detection system capable of measuring a wide energy region can be accomplished by distributing the direction of propagation of the diffracted X-rays by means of the splitter 50. The X-rays can be distributed to four or more positions by the splitter 50.

Third Embodiment

The configuration of an X-ray detection system according to a third embodiment is described by referring to FIGS. 4A-4D. In all the FIGS. 1-4D, like components are indicated by like reference numerals and repeated description thereof will be omitted.

The third embodiment is similar to the first and second embodiments except for the structure of the splitter 50 which distributes the imaging plane. That is, the splitter 50 shown in FIG. 4A distributes the direction of propagation of the diffracted X-rays coming from the diffraction grating 40 such that the imaging plane for the diffracted X-rays is assigned to three positions angularly spaced from each other by 120° within the imaging plane (XZ-plane).

The splitter 50 is configured including a tubular X-ray guiding mirror portion formed by mirrors 51 reflecting the diffracted X-rays, the mirror portion having an introduction portion 50A, a branching portion 50B, and branching output portions 50C1, 50C2, 50C3. The splitter 50 further includes a rotary selector shutter 55 (see FIGS. 4B-4D) transmitting the diffracted X-rays at any position to distribute the direction of propagation of the diffracted X-rays in the branching portion 50B of the tubular X-ray guiding mirror portion, a driving portion (not shown) for driving the shutter 55, and a control portion 54 giving an instruction to the driving portion to control the rotational phase of the shutter 55 according to various decision conditions.

Figure 4A:
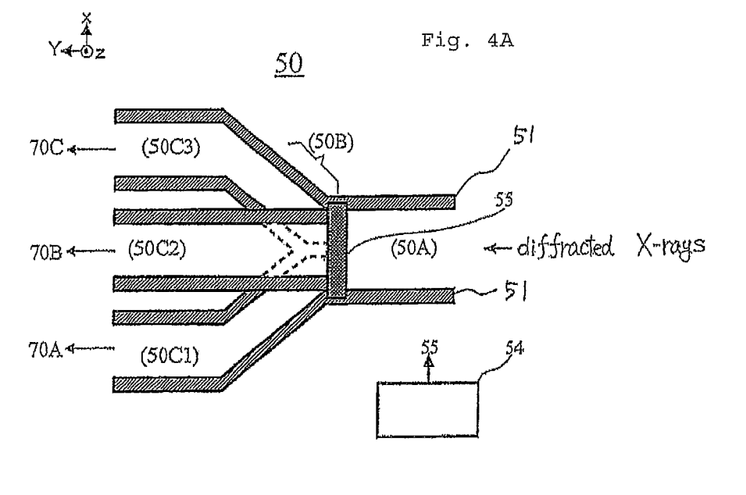
FIGS. 4A-4D show cross sections of main portions of an X-ray detection system according to an embodiment of the invention.

The image sensors 70A, 70B, and 70C of the image sensor arrangement 70 are three kinds of X-ray CCD cameras or X-ray CMOS cameras having high, moderate, and low energy sensitivities, respectively, to the soft X-rays in order to detect different energy regions of the diffracted X-rays. Preferably, each image sensor is made of a back-illuminated X-ray CCD camera. The position of the image sensor arrangement 70 is so adjusted that its light-sensitive surface is coincident with the imaging plane for the diffracted X-rays.

The image sensor 70A is mounted at the imaging plane of the splitter 50 on the side of the branching output portion 50C1. The image sensor 70B is mounted at the imaging plane of the splitter 50 on the side of the branching output portion 50C2. The image sensor 70C is mounted at the imaging plane of the splitter 50 on the side of the branching output portion 50C3. Image sensors different in energy sensitivity characteristics are arranged as the image sensors 70A-70C.

In the configuration described so far, the control portion 54 gives an instruction for rotation to the movable mirror driving portion by referring to decision conditions (such as energy value, kind of the used diffraction grating 40, material of the sample 20 (as to whether it easily produces cathodoluminescence), kind of the used X-ray window, and the ratio of signal intensity between characteristic X-rays and cathodoluminescent signal) and using predetermined decision conditions.

Figure 4B:
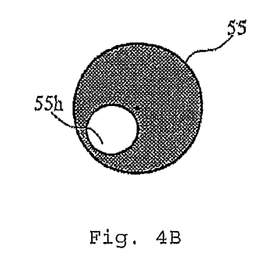
Figure 4C:
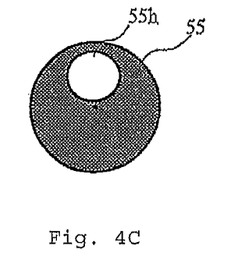

For example, where the control portion 54 has decided to perform a measurement using the image sensor 70A based on the above-described decision conditions, the control portion gives an instruction to the driving portion to align an opening 55h in the rotary selector shutter 55 with the branching output portion 50C1 as shown in FIG. 4B. Consequently, the diffracted X-rays entering from the introduction portion 50A of the splitter 50 are guided toward the branching output portion 50C1 from the branching portion 50B and focused onto the light-sensitive surface of the image sensor 70A. A spectrum of the X-rays diffracted and arising from the sample 20 is collected by the image sensor 70A and thus a measurement is performed.

Where the control portion 54 has decided to perform a measurement using the image sensor 70B based on the decision conditions described so far, the control portion gives an instruction to the driving portion to align the opening 55h in the rotary selector shutter 55 with the branching output portion 50C2 as shown in FIG. 4C. Consequently, the diffracted X-rays entering from the introduction portion 50A of the splitter 50 are guided toward the branching output portion 50C2 from the branching portion 50B and focused onto the light-sensitive surface of the image sensor 70B. A spectrum of the X-rays diffracted and arising from the sample 20 is collected by the image sensor 70B and thus a measurement is performed.

Figure 4D:
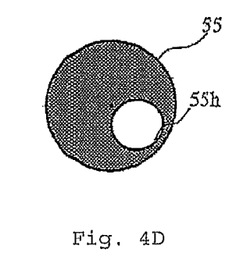

Furthermore, where the control portion 54 has decided to perform a measurement using the image sensor 70C based on the decision conditions described so far, the control portion gives an instruction to the driving portion to align the opening 55h in the rotary selector shutter 55 with the branching output portion 50C3 as shown in FIG. 4D. Consequently, the diffracted X-rays entering from the introduction portion 50A of the splitter 50 are guided toward the branching output portion 50C3 from the branching portion 50B and focused onto the light-sensitive surface of the image sensor 70C. A spectrum of the X-rays diffracted and arising from the sample 20 is collected by the image sensor 70C and thus a measurement is performed.

As described so far, image sensors having different energy sensitivity characteristics are arranged as the image sensors 70A, 70B, and 70C. An X-ray detection system capable of measuring a wide energy region can be accomplished by distributing the direction of propagation of the diffracted X-rays by means of the splitter 50 and the rotary selector shutter 55. The X-rays can be distributed to four or more positions by the splitter 50 and rotary selector shutter 55.

Fourth Embodiment

Figure 5:
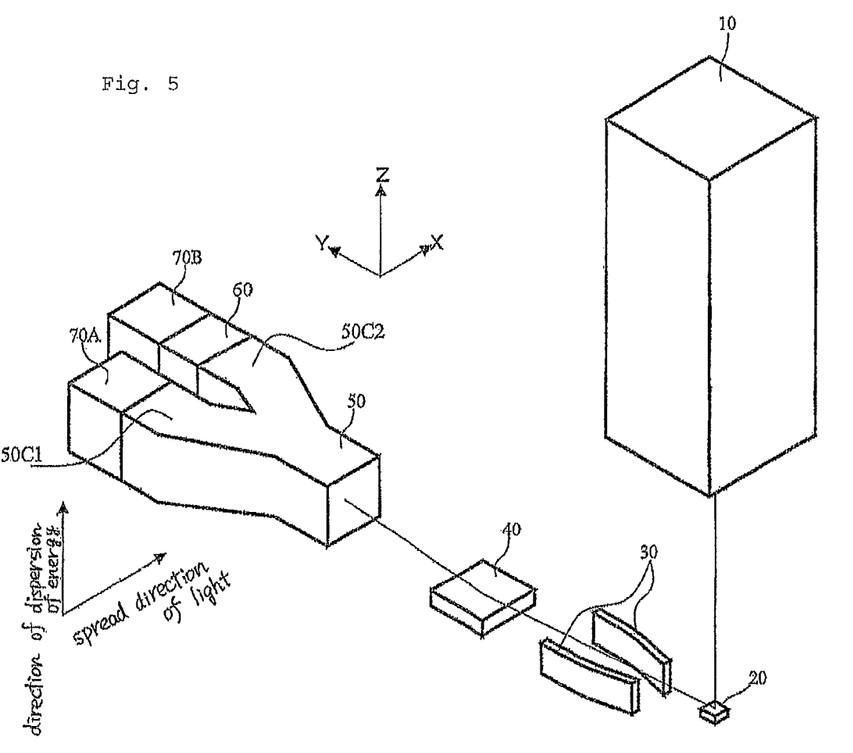
FIG. 5 is a perspective view of an X-ray detection system according to another embodiment of the present invention, showing the structure of the system.

The configuration of an X-ray detection system according to a fourth embodiment is described by referring to FIG. 5. In both FIGS. 1 and 5, like components are indicated by like reference numerals and repeated description thereof will be omitted.

The fourth embodiment is similar to the first embodiment except for the manner in which the image sensor arrangement 70 located behind the splitter 50 is connected. That is, in the fourth embodiment shown in FIG. 5, the electron beam irradiation portion 10, sample 20, X-ray gathering mirror portion 30, diffraction grating 40, splitter 50, and image sensor 70A of the splitter 50 on the side of one branching output portion 50C1 are identical with their counterparts.

On the other hand, a microchannel plate subassembly 60 is connected with the other branching output portion 50C2 of the splitter 50. The image sensor 70B is connected with the output side of the microchannel plate subassembly 60.

Characteristic X-rays emitted from the sample 20 irradiated with the electron beam are received by the diffraction grating 40. As a result, diffracted X-rays are produced. The direction of propagation of the diffracted X-rays is distributed by the splitter 50. Then, the input surface of the microchannel plate subassembly 60 is placed at the imaging surface for the diffracted X-rays. The image sensor 70B is placed on the output surface of the microchannel plate subassembly 60.

The microchannel plate subassembly 60 is made of a number of tiny photomultiplier tubes bound together. When soft X-rays are incident on the input surface, electrons are released and collide on the walls of the channels. The electrons are multiplied by the avalanche effect. As a result, the fluorescent screen on the output side fluoresces.

Therefore, there is disposed the image sensor 70B having sensitivity to the fluorescent light from the fluorescent screen on the output surface of the microchannel plate subassembly 60. Very high-sensitivity measurements are enabled by making use of the photomultiplication effect of the microchannel plate subassembly 60.

Figure 6:
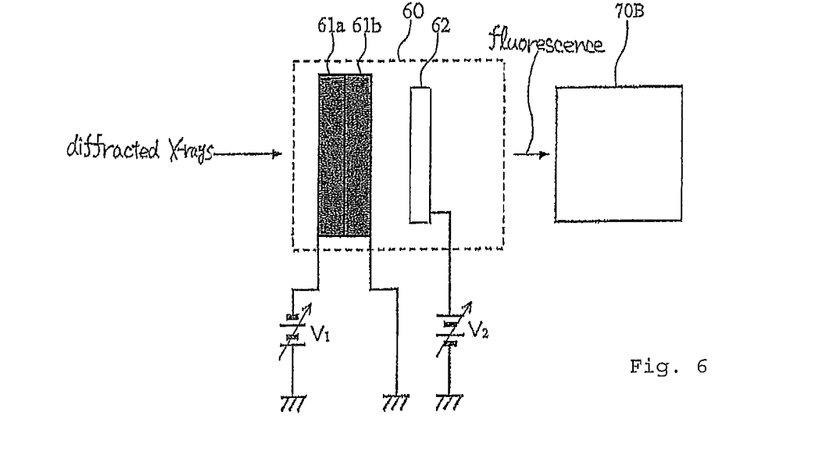
FIG. 6 is a circuit diagram partly in block form of a main portion of an X-ray detection system according to an embodiment of the invention.

FIG. 6 is a circuit diagram partly in block form of the microchannel plate subassembly 60 having the fluorescent screen, showing one example of the configuration of the subassembly. The microchannel plate subassembly 60 is made up of two stages of microchannel plates 61a and 61b for amplifying the diffracted X-rays. A fluorescent screen 62 that fluoresces in response to the output light from the microchannel plate 61b is disposed on the output side. The gain can be adjusted by varying the voltage $V_1$ applied to the microchannel plates 61a and 61b. The fluorescent state can be adjusted by varying the voltage $V_2$ applied to the fluorescent screen 62. The microchannel plates 61a and 61b provide a two-stage amplification which enables amplification at lower levels of noise than a single-stage voltage amplification.

In the configuration described so far, the control portion 54 gives operating instructions to the movable mirror driving portion 52 by referring to decision conditions (such as energy value, kind of the used diffraction grating 40, material of the sample 20 (as to whether it easily produces cathodoluminescence), kind of the used X-ray window, and the ratio of signal intensity between characteristic X-rays and cathodoluminescent signal) and using predetermined decision conditions.

An X-ray detection system capable of measuring a wide energy region can be accomplished by placing the image sensor 70A and the combination of the image sensor 70B and the microchannel plate subassembly 60 as described above and distributing the direction of propagation of the diffracted X-rays by means of the splitter 50. In addition, the microchannel plate subassembly 60 shown in this fourth embodiment can be utilized in any branching output portion of the splitter 50 of the second or third embodiment.

Fifth Embodiment

Figure 7:
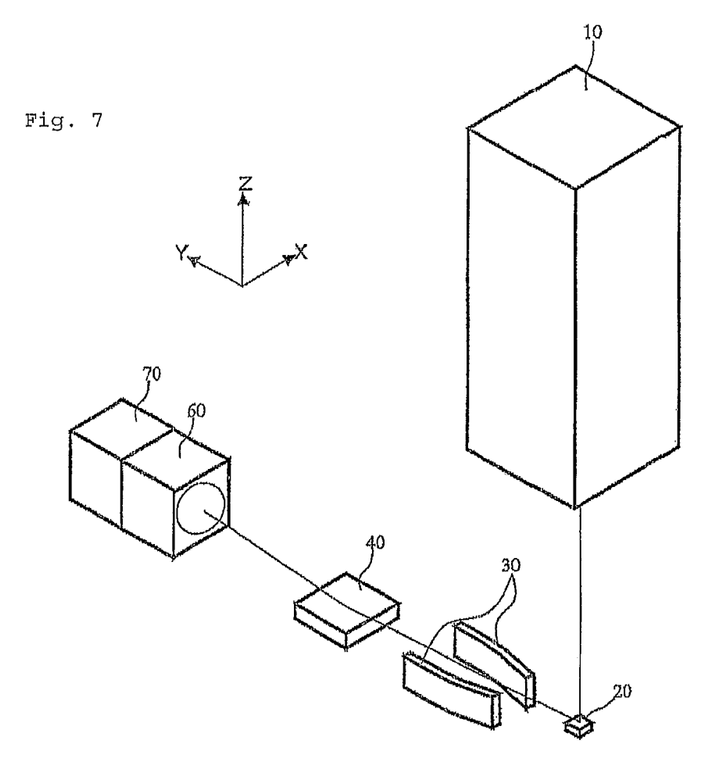
FIG. 7 is a perspective view of an X-ray detection system according to an embodiment of the invention, showing the state of the system.

The configuration of an X-ray detection system according to a fifth embodiment is described by referring to FIG. 7. In all of FIGS. 1, 5, and 7, like components are indicated by like reference numerals and repeated description thereof will be omitted.

This fifth embodiment is similar to the fourth embodiment except that the splitter 50 and the image sensor 70A are removed from the fourth embodiment using the microchannel plate subassembly 60. That is, in an X-ray detection system as described in the above-cited JP-A-2002-329473, the microchannel plate subassembly 60 is placed ahead of the image sensor arrangement 70.

In this embodiment, characteristic X-rays emitted from the sample 20 irradiated with the electron beam are received by the diffraction grating 40 to produce diffracted X-rays. The input surface of the microchannel plate subassembly 60 is placed at the imaging plane for the diffracted X-rays. There is disposed the image sensor arrangement 70 sensitive to the fluorescent light produced from the fluorescent screen on the output surface side of the microchannel plate subassembly 60. Very high-sensitivity measurements are enabled by making use of the photomultiplication effect of the microchannel plate subassembly 60.

Figure 8A:
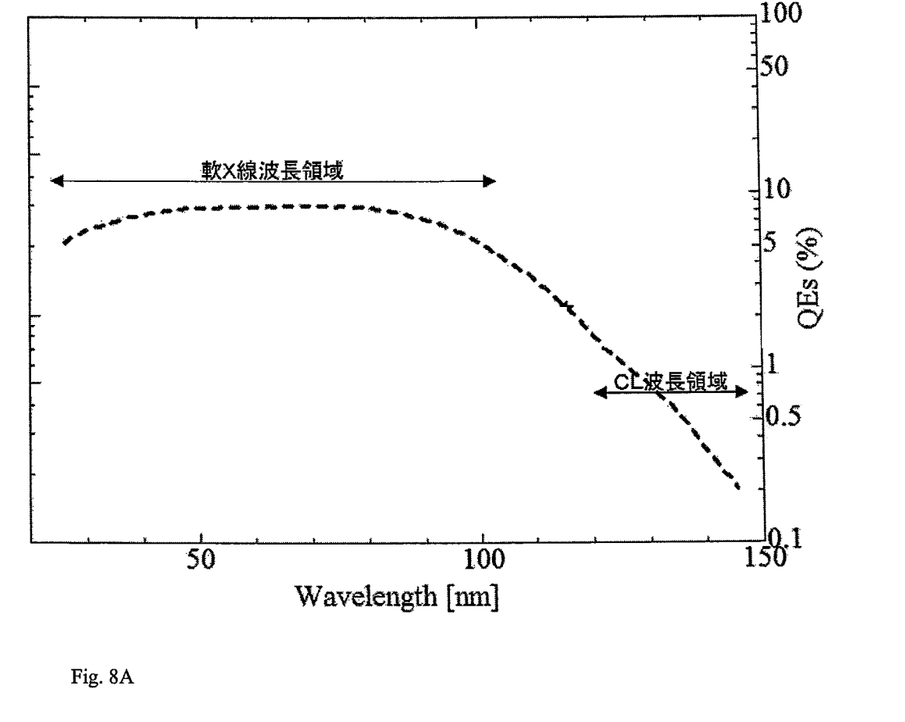
FIG. 8A is a graph illustrating the state of an X-ray detection system according to an embodiment of the invention.

As one example, the wavelength-quantization efficiency of the microchannel plate subassembly 60 is 8% in the soft X-ray wavelength range and 0.8% in the cathodoluminescent wavelength region as shown in FIG. 8A. Thus, there is an about 10 times difference. As a result, in an X-ray detection system in which the microchannel plate subassembly 60 is positioned immediately ahead of the image sensor arrangement 70, the resulting cathodoluminescence for soft X-rays can be reduced by a factor of 10. That is, the microchannel plate subassembly 60 has a higher quantization efficiency in the soft X-ray region than in the cathodoluminescent region. If cathodoluminescence occurs, the ratio of the X-rays impinging on the image sensor arrangement 70 can be increased.

Figure 8B:
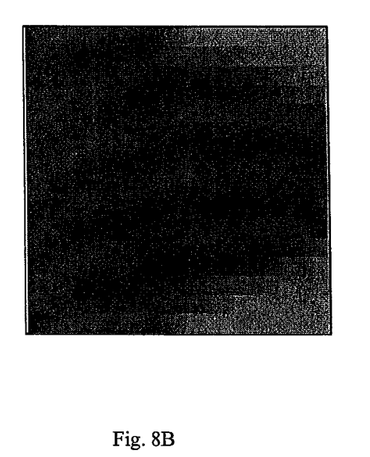
FIGS. 8B and 8C are diagrams portraying the results of measurements.
Figure 8C:
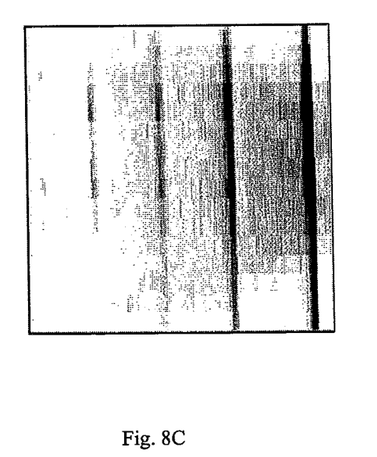

We made a measurement of diffracted X-rays under the influence of stray light such as cathodoluminescence. The results are portrayed in FIG. 8B. In contrast, a measurement of diffracted X-rays involving a reduction of cathodoluminescence owing to the microchannel plate subassembly 60 of the fifth embodiment was made under the same conditions (i.e., the manner in which the sample 20 is irradiated with an electron beam and use of the diffraction grating 40). In spite of the same conditions, very clear diffracted light (energy distribution) could be confirmed as shown in FIG. 8C.

In the fifth embodiment, the splitter 50 is not used. Where the splitter 50 and microchannel plate subassembly 60 are used as in the fourth embodiment, X-rays can be detected while reducing the effects of straight light such as cathodoluminescence in a similar manner.

Sixth Embodiment

Figure 9:
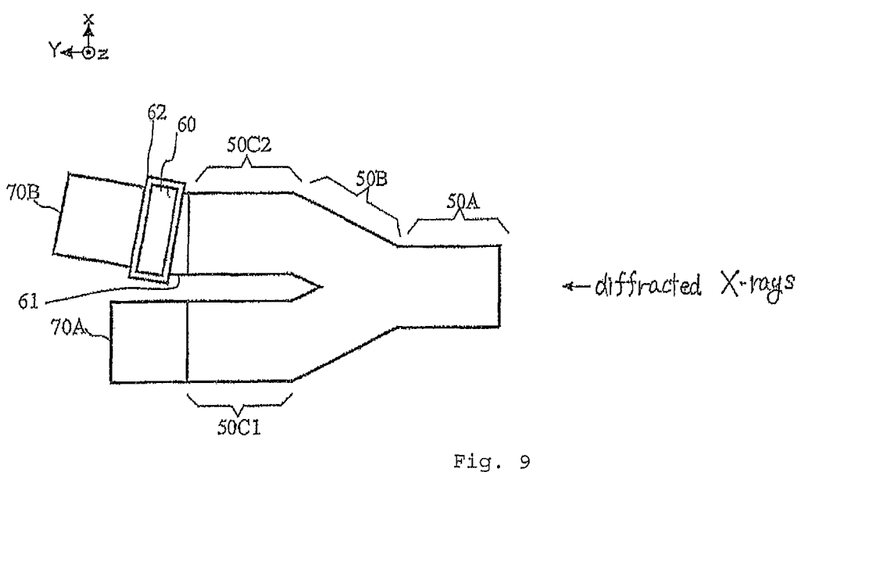
FIG. 9 is a side elevation of an X-ray detection system according to an embodiment of the invention, showing the structure of the system.

The configuration of an X-ray detection system according to a sixth embodiment is described by referring to FIG. 9. In FIG. 9 and other figures, like components are indicated by like reference numerals and repeated description thereof will be omitted.

In this sixth embodiment, the microchannel plate subassembly 60 is placed immediately ahead of the image sensor 70B in the same way as in the fourth embodiment.

A tiltably holding tubular portion 61 that holds the microchannel plate subassembly 60 at an angle to the direction of propagation of the diffracted X-rays is disposed. The holding portion 61 is made of a mirror that reflects X-rays. The holding portion 61 may be integrated with the branching output portion 50C2. That is, the end surface of the branching output portion 50C2 on the output side may be tilted. Furthermore, a rotatably holding portion 62 permitting the microchannel plate subassembly 60 to be held rotatably is disposed. The tiltably holding portion 61 and rotatably holding portion 62 may be integrated as a tiltably-and-rotatably holding portion. Additionally, a rotation control portion (not shown) for rotating the microchannel plate subassembly 60 at a given rotational angle is mounted.

Generally, each of the multiple tiny photomultiplier tubes constituting the microchannel plate subassembly 60 has a slight tilt angle, known as a bias angle. The sensitivity depends on the angle of incidence of impinging X-rays. Accordingly, the diffracted X-rays can be made to enter the microchannel plate subassembly 60 at an angle at which an optimum sensitivity is imparted to the subassembly 60, by determining the tilt angle of the tiltably holding portion 61 so as to cover the bias angle of the photomultiplier tubes of the microchannel plate subassembly 60 and rotating the subassembly 60 while tilted.

In the sixth embodiment, the microchannel plate subassembly 60 is shown to be disposed on the side of the branching output portion 50C2 of the splitter 50. Even in an X-ray detection system not using the splitter 50 as in the fifth embodiment, good sensitivity characteristics can be obtained by rotating the microchannel plate subassembly 60 while at an angle.

Seventh Embodiment

Figure 10A:
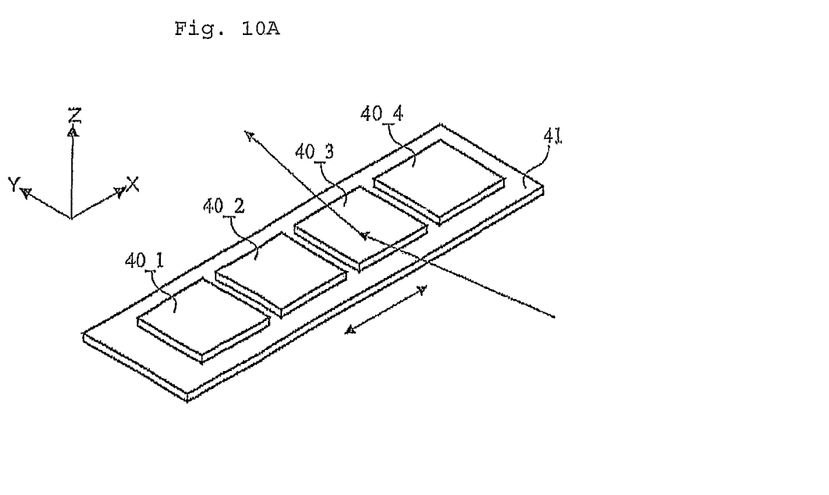
FIGS. 10A and 10B show perspective views of an X-ray detection system according to an embodiment of the invention, showing the structure of the system.
Figure 10B:
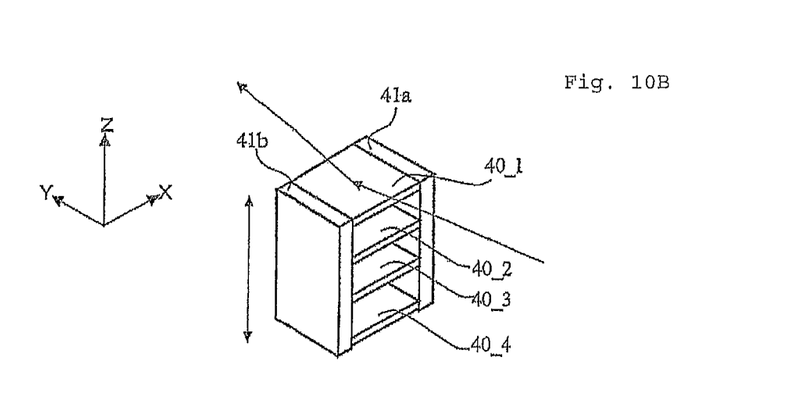

The configuration of an X-ray detection system according to a seventh embodiment is described by referring to FIGS. 10A-10B. In the seventh embodiment, plural diffraction gratings 40_1 to 40_4 can be selected. The seventh embodiment can be applied to each of the first through sixth embodiments.

In the various embodiments described above, an X-ray detection system capable of measuring a wide energy region can be accomplished by selectively using plural image sensors (such as 70A and 70B) having different energy sensitivity characteristics through the use of the splitter 50 or by using the microchannel plate subassembly 60.

Therefore, it is desirable to be capable of accommodating variations in the required resolution and in the range of the measured energy by selectively using plural diffraction gratings 40_1 to 40_4 according to such a measurement of a wide energy region.

As shown in FIG. 10A, a diffraction grating holding portion 41 capable of moving in the X-direction and plural diffraction gratings 40_1, 40_2, 40_3, and 40_4 arranged planarly in the X-direction on the holding portion 41 are prepared. The diffraction gratings 40_1 to 40_4 are controllably driven in the X-direction by a drive mechanism and a control portion (none of which are shown) such that any one of the gratings 40_1 to 40_4 diffracts characteristic X-rays emanating from the sample 20. Consequently, an appropriate one can be selected from the diffraction gratings 40_1 to 40_4 and used according to a measurement of a wide energy range.

As shown in FIG. 10B, diffraction grating holding portions 41a and 41b capable of moving in the Z-direction and plural diffraction gratings 40_1, 40_2, 40_3, and 40_4 laminated in the Z-direction and held by the holding portions 41a and 41b are prepared. The diffraction gratings 40_1 to 40_4 are controllably driven by a drive mechanism and a control portion (none of which are shown) such that any one of the gratings diffracts characteristic X-rays produced from the sample 20. Consequently, an appropriate one can be selected from the diffraction gratings 40_1 to 40_4 and used according to a measurement of a wide energy range.

In the geometry of FIG. 10B, if openings are formed on the incident side and exit side, respectively, of the lamination of the diffraction gratings 40_1 to 40_4, the diffraction grating holding portions may be varied in shape.

The four diffraction gratings 40_1 to 40_4 shown in FIGS. 10A and 10B merely give an example of usage of diffraction gratings. Two, three, five, or more diffraction gratings can be selectively used. Where two diffraction gratings are used, the used grating can be switched by sticking the gratings on the opposite surfaces of the diffraction grating holding portion 41 (FIG. 10A) and inverting the holding portion 41.

What is claimed is:

1. An X-ray detection system comprising:
   electron beam irradiation means for irradiating a sample with an electron beam;
   a diffraction grating that receives characteristic X-rays emitted from the irradiated sample and produces diffracted X-rays;
   a splitter for distributing a direction of propagation of the diffracted X-rays such that an imaging plane for the diffracted X-rays is assigned to plural positions spaced apart in a direction perpendicular to a direction of energy dispersion of the diffracted X-rays; and
   plural image sensors having a higher energy sensitivity and a lower energy sensitivity, respectively, and disposed respectively at the plural positions to which the imaging plane is assigned,
   wherein said splitter has a tubular X-ray guiding mirror portion made by mirrors for reflecting the diffracted X-rays, a movable mirror for distributing the direction of propagation of the diffracted X-rays in a branching portion of the guiding mirror portion, and a movable mirror controller for controlling a position of the movable mirror.

2. An X-ray detection system as set forth in claim 1, wherein said image sensor having said higher energy sensitivity is an X-ray image sensor, and wherein said image sensor having said lower energy sensitivity is an image sensor having a microchannel plate subassembly on its light-sensitive surface.

3. An X-ray detection system as set forth in claim 2, wherein said microchannel plate subassembly has a higher quantization efficiency in a soft X-ray region than in a cathodoluminescence region.

4. An X-ray detection system as set forth in any one of claims 2 or 3, further comprising: a tiltably-and-rotatably holding portion for holding the microchannel plate subassembly such that the subassembly is rotatable while being tilted relative to the direction of propagation of the diffracted X-rays; and a rotation control portion for rotating the microchannel plate subassembly while the subassembly is held by the tiltably-and-rotatably holding portion.

5. An X-ray detection system as set forth in any one of claims 1, 2, or 3, wherein said diffraction grating is a varied line-space (VLS) diffraction grating.

\* \* \* \* \*